United States Patent [19]
Carpenter, Jr. et al.

[11] Patent Number: 5,324,824
[45] Date of Patent: Jun. 28, 1994

[54] METAL-ISONITRILE ADDUCTS FOR PREPARING RADIONUCLIDE COMPLEXES

[75] Inventors: Alan B. Carpenter, Jr., Tyngsboro; Leo J. Maheu, Andover; Michael A. Patz, Somerville, all of Mass.; Thomas H. Tulip, Nashua, N.H.; Karen E. Linder, Somerville, Mass.; Vinayakam Subramanyam, Towson, Md.; Jeffery S. Thompson, Wilmington, Del.

[73] Assignee: The DuPont Merck Pharmaceutical Co., Wilmington, Del.

[21] Appl. No.: 670,458

[22] Filed: Mar. 12, 1991

Related U.S. Application Data

[60] Continuation of Ser. No. 411,024, Nov. 15, 1989, abandoned, which is a division of Ser. No. 880,349, Jun. 25, 1986, Pat. No. 4,894,445, which is a continuation-in-part of Ser. No. 762,392, Aug. 5, 1985, abandoned.

[51] Int. Cl.$^5$ ............ C07C 13/00; A61K 43/00; B65D 69/00
[52] U.S. Cl. ............................ 534/14; 206/569
[58] Field of Search .................. 424/1.1; 534/14; 206/569

[56] References Cited

U.S. PATENT DOCUMENTS

| | | | |
|---|---|---|---|
| 4,707,544 | 11/1987 | Jones | 534/14 |
| 4,735,793 | 8/1985 | Jones | 424/1.1 |
| 4,894,445 | 1/1990 | Carpenter | 534/14 |

*Primary Examiner*—Robert L. Stoll
*Assistant Examiner*—C. Harris
*Attorney, Agent, or Firm*—Gerald J. Boudreaux

[57] ABSTRACT

A method for preparing a coordination complex of an isonitrile ligand and a radioisotope of Tc, Ru, Co, Pt, Re, Os, Ir, W, Re, Cr, Mo, Mn, Ni, Rh, Nb and Ta from a non-radioactive metal adduct of the isonitrite.

5 Claims, No Drawings

METAL-ISONITRILE ADDUCTS FOR PREPARING RADIONUCLIDE COMPLEXES

This application is a continuation of application Ser. No. 07/411,024 filed Nov. 15, 1989 abandoned which is a division of application Ser. No. 06/880,349, filed Jun. 25, 1986, U.S. Pat. No. 4,894,445, which is a continuation-in-part of application Ser. No. 762,392, filed Aug. 5, 1985 (now abandoned).

FIELD OF THE INVENTION

This invention relates to isonitrile complexes of radionuclides, for example, of radioactive isotopes such as, $^{99m}Tc$, $^{99}Tc$, $^{97}Ru$, $^{51}Cr$, $^{57}Co$, $^{188}Re$, and $^{191}Os$, and particularly to metal-isonitrile adducts for making such radionuclide complexes.

BACKGROUND OF THE INVENTION

A variety of radioisotope imaging and labeling agents have been developed in the past; however, certain of the materials previously available have generally suffered from the shortcomings of high cost, complexity of the method of preparation, or failure to exhibit high quality imaging or highly effective labeling.

Isonitrile complexes of various non-radioactive metals have been described. Oxine complexes of $^{99m}Tc$ have been described for use in labeling platelets. Wistow et al., *J. Nucl. Med.*, Vol. 19, 483–487 (1978). The direct labeling of red blood cells with $^{99m}Tc$ by a reductive process, and the use of the labeled cells for imaging have been described. Smith et al., *J. Nucl. Med.*, Vol. 17, 127–132 (1976). Various complexes of $^{99m}Tc$ with arsenic- and phosphorus-containing organic compounds have been proposed for use as imaging and labeling agents. Deutsch et al., *Science*, Vol. 214, 85–86 (1981); *J. Nucl. Med.*, Vol. 22, 897–907 (1981); European Pat. Appln. No. 81400618.5, published Oct. 28, 1981, Publn. No. 01538756.

U.S. Pat. No. 4,452,774 describes a coordination complex of an isonitrile ligand with a radioactive metal (radionuclide) selected from the class consisting of radioactive isotopes of Tc, Ru, Co, Pt, Fe, Os, Ir, W, Re, Cr, Mo, Mn, Ni, Rh, Pd, Nb, and Ta, and methods for using such complexes. Preferably, the isonitrile complexes comprise one of the above radioactive metals wherein each available coordination site is filled with an isonitrile ligand. The isonitrile ligand can be either monodentate or polydentate such as, for example, bidentate or tridentate. Also described is a kit comprising an isonitrile ligand and a reducing agent capable of reducing the radioactive metal to form the coordination complex.

Because of the general availability of supplies of $^{99m}Tc$ in clinical laboratories in the form of pertechnetate as well as the desirable half-life and gamma ray energy of this radionuclide, the complexes preferably contain $^{99m}Tc$, although complexes with other radionuclides are also described. Moreover, the general availability of supplies of pertechnetate make it convenient to use kits for preparation of various complexes of $^{99m}Tc$.

The isonitrile complexes can readily be prepared and isolated at both macro and tracer concentration in aqueous media, together with any of a wide variety of counterions, as appropriate. They display effective labeling characteristics for liposomes or vesicles, and a variety of living cells containing lipid membranes, and are also effective imaging agents for detecting abnormalities in the tissues of various organs, particularly in the heart, as well as the existence of blood clots. The complexes of $^{99m}Tc$ are particularly preferred because of the desirable nuclear properties of this radioisotopes, i.e., its half-life and gamma ray energy.

One problem encountered in preparing the isonitrile complexes described in U.S. Pat. No. 4,452,774 is that many isonitrile ligands are extremely volatile. Thus, the isonitrile ligand is difficult to handle, and lyophilized kits are not practical. Therefore, new and better ways for handling the isonitrile ligands for making radionuclide complexes are being sought.

SUMMARY OF THE INVENTION

Certain of the above problems can be overcome by preparing soluble metal-adducts of isonitrile ligands and using the metal-isonitrile adduct to prepare the desired radionuclide-isonitrile complex. Surprisingly, metals that do form adducts of the isonitriles such as manganese, iron, and ruthenium have not been successfully replaced from their isonitrile adducts (or salts) by, for instance, technetium to form the desired radionuclide complex with the isonitrile.

Therefore, the present invention provides a method for joy, preparing a radionuclide coordination complex of an isonitrile ligand and a radioactive metal selected from the class consisting of radioactive isotopes of Tc, Ru, Co, Pt, Fe, Os, Ir, W, Re, Cr, Mo, Mn, Ni, Rh, Pd, Nb and Ta, said method comprising forming a soluble metal adduct of said isonitrile ligand by admixing said ligand with a complex of a displaceable metal selected from the class consisting of Cu, Mo, Pd, Co, Ni, Cr, Ag and Rh to form a soluble metal-isonitrile complex, and admixing said metal-isonitrile complex with said radioactive metal in a suitable solvent to replace said displaceable metal with the radioactive metal.

DETAILED DESCRIPTION OF THE INVENTION

The metal-isonitrile adducts of the instant invention are reacted with a radioactive isotope selected from the list above to form the desired radionuclide complex. The metals useful in the practice of this invention are selected from the class consisting of Cu, Mo, Pd, Co, Ni, Cr, Ag and Rh.

Any isonitrile ligand can be used in the practice of this invention. Suitable isonitrile ligands include those having, for example, the formula CNR where the organic radical R can be aliphatic or aromatic and may be substituted with a variety of groups which may or may not be charged. Among the aromatic R groups which may be present are phenyl, tolyl, xylyl, naphthyl, biphenyl and substituted aromatic groups containing such substitutents as halo (e.g., chloro, bromo, iodo or fluoro), hydroxy, nitro, alkyl, alkyl ether, alkyl ester, etc.; among the aliphatic R groups which may be present are alkyl, preferably containing 1 to 20 carbon atoms, such as methyl, ethyl, n-propyl, isopropyl, n-butyl, t-butyl, isobutyl, n-hexyl, 2-ethylhexyl, dodecyl, stearyl, etc. Substituent groups may also be present in the aliphatic groups, including among others the same substituent groups as those listed above for aromatic groups.

The lipophilic characteristics of the complex can be varied by varying the R groups to adapt the complex for labeling selected materials, for membrane transport such as for the blood-brain barrier, or for imaging selected organs and dynamic processes related to their function (e.g. heart function).

The metal-isonitrile adducts of the present invention can readily be prepared by admixing a complex of the displaceable metal and the isonitrile ligand in a suitable media at temperatures from room temperature to reflux temperature or even higher. The reaction is generally complete after about 1 minute to about 2 hours, depending upon the reagents employed and the conditions used.

Any desired counterion may also be present in the composition, such as nitrate, sulfate, chloride, fluoride, bromide, iodide, tetrafluoroborate, hexafluorophosphate, trifluoromethane sulfonate, etc.

The desired labeled radionuclide isonitrile complexes are prepared from the metal-isonitrile adducts by admixing the adduct with the radioactive metal in suitable media at temperatures from room temperature to reflux temperatures or even higher. The desired labeled isonitrile complexes are isolable and can be obtained in high yields. In some cases the metal-isonitrile adduct can itself act as a reducing agent thus eliminating the need for an additional reducing agent. Additional reducing agents, when required or desired to speed up the reaction, are well known to those skilled in the art. Examples of such well-known reducing agents include stannous salt (often used in the form of kits), formamidine sulfinic acid, sodium dithionite, sodium bisulfite, hydroxylamine, ascorbic acid, and the like. The reaction is generally complete after about 1 minute to about 2 hours, depending upon the particular reagents employed and the conditions used. The yield of labelled radionuclide isonitrile complex is about 45%, preferably at least 70%, and more preferably at least 90% of the radioactive nuclide used for labeling.

In the case of technetium such as, for example $^{99}$Tc or $^{99m}$Tc, an isonitrile complex is preferably made by mixing an appropriate reducing agent (capable of reducing technetium in aqueous medium) and the appropriate metal-isonitrile adduct, then adding pertechnetate. Alternatively, the metal adduct and pertechnetate are mixed, then reductant added. The presently preferred displaceable metals for use when preparing a technetium-isonitrile complex in accord with the present invention are copper, cobalt and nickel.

The isonitrile technetium complexes prepared in accord with this invention can also be prepared from preformed technetium complexes having oxidation states for technetium of, for instance, III, IV or V, by treating these preformed complexes with an excess of metal-isonitrile adduct under suitable conditions. For example, the technetium-isonitrile complex can also be prepared by reacting the desired metal-isonitrile adduct with the hexakis-thiourea complex of Tc$^{III}$ or with a technetium-glucoheptonate complex, or the like.

An excess of the metal-isonitrile adduct, up to 1 to 100 fold molar excess or more, and an excess of reducing agent, can be used in the complexing reaction to ensure maximum yield from the technetium. Following the reaction, the desired complex can be separated from the reaction mixture, if required, for example, by crystallization or precipitation or by conventional chromatography or ion exchange chromatography; see U.S. Pat. No. 4,452,774, supra, the disclosure of which is hereby incorporated by reference.

Kits in accord with the present invention comprise an adduct of a displaceable metal (as listed above) and an isonitrile ligand and, if required, a quantity of a reducing agent for reducing a preselected radionuclide. Preferably, such kits contain a predetermined quantity of a metal isonitrile adduct and a predetermined quantity of a reducing agent capable of reducing a predetermined quantity of the preselected radionuclide. It is also preferred that the isonitrile ligand and reducing agent be lyophilized, when possible, to facilitate storage stability. If lyophilization is not practical, the kits are stored frozen. The metal-isonitrile adduct and reducing agent are preferably contained in sealed, non-pyrogenic, sterilized containers.

In one embodiment of the invention, a kit for use in making the radionuclide complexes in accord with the present invention from a supply of $^{99m}$Tc such as the pertechnetate solution in isotonic saline (available in most clinical laboratories) includes the desired quantity of a selected isonitrile ligand in the form of a metal-isonitrile adduct to react with a predetermined quantity of pertechnetate, and a predetermined quantity of reducing agent such as, for example, stannous ion in the form of stannous glucoheptonate to reduce the predetermined quantity of pertechnetate to form the desired technetium-isonitrile complex.

Isonitrile complexes prepared in accord with this invention can be used to label human erythrocytes (red blood cells); to measure lung function; to measure hepatobiliary function; and for myocardial imaging. For instance, both t-butyl and isopropyl isonitrile products have been used to visualize myocardial tissue by external imaging.

Cells can be readily labeled by incubating the radiolabeled complexes of this invention with such cells in a suitable medium and measuring the uptake of radioactivity in accord with the methods described by Kassis, A. I. et al., *J. Nucl. Med.*, Vol. 21, 88–90 (1980). Incorporation of the radioactive complex can be as high as 29 pCi/cell. Studies have shown that the radioactive label can be 90% retained for up to sixteen hours. Autologous leukocytes separated from fresh rabbit blood were labeled with the $^{99m}$Tc complex and subsequently reinjected into the rabbit. The distribution of the radiolabeled cells could be followed by gamma camera.

The choice of radionuclides will depend on the use. For example, preferred radionuclides for diagnostic imaging are radioactive isotopes of Tc, Ru, Co, Pt, Fe, Os, and Ir; preferred radionuclides for therapeutic uses are radioactive isotopes of W, Re, Fe, and Os; preferred radionuclides for radioactive tagging are Cr, Mo, Co, Tc, Fe, Mn, W, Ru, Ni, Rh, Ir, Pd, Nb, and Ta.

This invention has been described in detail including the preferred embodiments thereof. However, it will be appreciated that those skilled in the art, upon consideration of this disclosure, may make modifications and improvements within the spirit and scope of this invention.

EXAMPLES

EXAMPLE 1

Preparation of [Cu(CN-t-Bu)$_4$]NO$_3$

Under an inert atmosphere, 2.64 g (10.9 mmol) cupric nitrate, CU(NO$_3$)$_2$.3H$_2$O, and 2.10 g (33.0 mmol) copper dust are stirred in 25 mL predried methanol until dissolved; 10 mL (88.4 mmol) of t-butyl isonitrile is added and the mixture stirred for four hours. Excess copper metal is removed by filtration under nitrogen and then the solvent is removed under high vacuum. The resulting solid is dissolved in 10 mL methanol and filtered. The product is precipitated with the addition of diethyl ether. The white solid is dried in vacuo at ambient temperature to produce the desired complex in 65% yield.

EXAMPLE 2

Preparation of [Cu(CN-t-B)$_4$]Cl

Under dry N$_2$ or an appropriate inert atmosphere, a suspension of 1.0 g (10.1 mmol) of CuCl in 100 mL of CHCl$_3$ is treated with 6.8 mL (5.0 g, 60.1 mmol) of t-butyl isonitrile. The mixture warms slightly and is allowed to stir for 1 hour. The solution is then filtered to remove any unreacted CuCl, and the CHCl$_3$ solution reduced to 10–15 mL on a rotary-evaporator. To the reduced solution is then added 75–100 mL of diethyl ether (anhydrous). The colorless solid is then isolated by filtration on a glass frit. The isolated solid is then washed with diethyl ether (anhydrous) 3×50 mL, and allowed to dry. The yield of the desired product is about 75%.

EXAMPLE 3

Preparation of [MoCl(CN-t-Bu)$_6$]Cl

The desired complex is synthesized in two steps from commercially available cycloheptatriene molybdenum tricarbonyl via the intermediate MO(CO) (CN-t-Bu )$_3$ under an inert atmosphere using thoroughly dried glassware and solvents. 3.90 g (46.96 mmol) of CN-t-Bu is added to a solution of 3.0 g (11.45 mmol) cycloheptatriene molybdenum tricarbonyl in 30 mL of methylene chloride. The solution is stirred for 18 hours and concentrated to dryness to obtain approximately 4.70 g (96% yield) of tris-(t-butyl isonitrile) molybdenum tricarbonyl. 2.50 g (5.82 mmol) of this intermediate is dissolved in 75 mL of toluene and the resulting mixture is treated sequentially with 1.65 g (18.04 mmol) of t-butyl isonitrile and 1.85 g (6.73 mmol) of iodosylbenzene dichloride. The solution is stirred for 18 hours to assure complete evolution of carbon monoxide and the desired product isolated by filtration to realize approximately 3.21 g (83% yield). The material is recrystallized from acetone/diethyl ether or methylene chloride/pentane mixtures.

EXAMPLE 4

Preparation of cis-PdCl$_2$(CN-t-Bu)$_2$

To a 50 mL round bottom flask is added 250 mg (1.41 mmol) of PdCl$_2$, 10 mL of acetone, 312 μL (229 mg, 2.75 mmol) of t-butyl isonitrile, and a stir bar. The mixture is stirred at 25° C. for 3 hours after which time the solution is colorless. The crude product is precipitated by the addition of 20 mL of water and filtered. Recrystallization from hot acetone yields 283 mg (77%) of cis-PdCl$_2$(CN-t-Bu)$_2$ as pale yellow flakes.

EXAMPLE 5

Preparation of [Co(CN-t-Bu)$_5$[CF$_3$SO$_3$

The desired complex is obtained by first preparing [Co(H$_2$O)][CF$_3$SO$_3$]$_2$ followed by reaction with the t-butyl isonitrile ligand. To 2.2 g (9.25 mmol) of [Co(H$_2$O)$_6$]Cl$_2$ (in a 100 mL three-neck round-bottom flask fitted with a condenser, thermometer, and nitrogen purge tube) is slowly added 10 ml of CF$_3$SO$_3$H with stirring. The mixture is then heated using a heating mantle to 100°–71.10° C. under a moderate N$_2$ purge to remove the HCl produced. After 2 hours, 10 mL of ethanol is carefully added to produce a blue solution. Heating is continued with the N$_2$ purge for an additional 1 hour, after which time the solution is pink and contains only a small amount of undissolved solid. The mixture is cooled to room temperature and the resulting pink precipitate filtered on a glass frit, washed with diethyl ether, and air dried. Yield: 2.3 g (53%).

A solution of 0.5 g (1.08 mmol) of [Co(H$_2$O)$_6$][[CF$_3$SO$_3$]$_2$ in 50 mL of ethanol is treated with 1.0 mL (0.735 g, 8.8 mmol) of t-butyl isonitrile. The mixture is stirred and warmed gently for 30 minutes or until all solids have dissolved, and then 2 mL of a 4% ethanolic N$_2$H$_4$solution is added dropwise with stirring. The color of the solution changes from blue to yellow-brown. The solvent is removed on a rotary evaporator and the residue is dissolved in 20 mL of methylene chloride and passed through a 1" plug of neutral alumina in fritted glass funnel. A yellow solution is collected with continued elution of methylene chloride, and this solution was evaporated to dryness to yield 0.42 g (63%) of yellow, crystalline [Co(CN-t-Bu)$_5$]CF$_3$SO$_3$.

EXAMPLE 6

Preparation of [Ni(CN-t-Bu)$_4$](BF$_4$)$_2$

To a vigorously stirred solution of 0.5 g (1.47 mmol) of [Ni(H$_2$O)$_6$](BF$_4$)$_2$ in 40 mL of 1:1 (v/v) ethanol-diethyl ether is added 0.75 mL (0.56 g, 6.74 mmol) of t-butyl isonitrile. From the resulting orange solution appears an orange-tan precipitate. The solution is then stirred for ten minutes and the precipitate filtered, washed with diethyl ether (2×10 mi), and air dried. Yield: 0.79 (95%).

EXAMPLE 7

Preparation of [Cr(CN-t-Bu)$_6$][PF$_6$]$_2$

Under a inert atmosphere, 3.08 g (16.3 mmol) of potassium hexafluorophosphate is combined with 4.74 g (57.0 mmol) of t-butyl isonitrile in 30 mL of absolute ethanol. To this mixture is added 1.0 g (8.14 mmol) of chromous chloride as a 70 mL absolute ethanolic solution. The solution is stirred for two hours and the yellow-green product is isolated by filtration of the resulting suspension. The solid is washed twice with 30 mL of absolute ethanol and dried to obtain approximately 6.59 g (96% yield) of the desired complex.

EXAMPLE 8

Preparation of [Ag(CN-t-Bu)$_4$]NO$_3$

In a clean, dry round bottom flask, 1.0 g (5.89 mmol) of silver nitrate is dissolved in 25 mL of absolute ethanol and the solution is treated with 2.94 g (35.4 mmol) of t-butyl isonitrile. The solution is stirred under inert atmosphere for four hours in the absence of light. The resulting solution is concentrated to dryness and 2.31 g (78% yield) of vacuum-dried product is obtained.

EXAMPLE 9

Preparation of [Rh(CN-t-Bu)$_4$]Cl

Under an inert atmosphere, 1.00 g (2.57 mmol) of bis(ethylene)rhodium chloride dimer is stirred in 50 mL of dry toluene in a 100 mL round-bottomed flask. Added dropwise to the resulting suspension is 1.2 g (14.4 mmol) t-butyl isonitrile and the solution is stirred for 5 minutes. The solution is filtered to remove insolubles and an additional 1.3 g (15.6 mmol) of t-butyl isonitrile is added to the filtrate. After stirring vigorously for 30 minutes the solution is filtered and the collected solid washed with 2×20 mL dry n-hexane. The solid is dried in vacuo at ambient temperature to constant weight to produce the desired complex in 90-95% yield.

We claim:

1. A lyophilized kit for preparing a coordination complex of an isonitrile ligand and a radionuclide selected from the class consisting of radioactive isotopes of Tc, Ru, Co, Pt, Fe, Os, Ir, W, Re, Cr, Mo, Mn, Ni, Rh, Pd, Nb, and Ta, said kit comprising a lyophilized predetermined quantity of (a) an adduct of a complex of copper and said isonitrile ligand and (b) a predetermined quantity of a reducing agent capable of reducing a predetermined quantity of a preselected one of said radionuclides to form said complex by replacing the copper from said ligand with said radionuclide.

2. The kit of claim 1 wherein the radionuclide is Tc-99m.

3. The kit of claim 1 wherein the isonitrile ligand has the formula CNR where R is butyl or butyl having an alkyl ether or alkyl ester substitution.

4. The kit of claim 1 wherein the reducing agent is stannous ion.

5. The kit of claim 1 in a sealed, non-pyrogenic sterilized container.

* * * * *